(12) United States Patent
Sakurai et al.

(10) Patent No.: US 6,544,535 B2
(45) Date of Patent: Apr. 8, 2003

(54) COMPOSITION FOR IMPROVING COOLING SENSATION EFFECTS

(75) Inventors: Kazutoshi Sakurai, Hiratsuka (JP); Kenichiro Shiroyama, Hiratsuka (JP)

(73) Assignee: Takasago International Corp., Tokyo (JP)

(*) Notice: Subject to any disclaimer, the term of this patent is extended or adjusted under 35 U.S.C. 154(b) by 0 days.

(21) Appl. No.: 09/974,723

(22) Filed: Oct. 10, 2001

(65) Prior Publication Data

US 2002/0090351 A1 Jul. 11, 2002

(51) Int. Cl.[7] .............................. A61K 9/00; A61K 6/00; A61K 7/08; A61K 7/06
(52) U.S. Cl. .................... 424/401; 424/400; 424/70.27; 424/70.01
(58) Field of Search ................................ 424/401, 400, 424/70.27

(56) References Cited

U.S. PATENT DOCUMENTS 6,252,003 B1 * 6/2001 Kuwahara et al. .......... 525/242
6,328,982 B1 * 12/2001 Shiroyama et al. ......... 424/401

* cited by examiner

Primary Examiner—Theodore J. Criares
Assistant Examiner—Jennifer Kim
(74) Attorney, Agent, or Firm—Darby & Darby

(57) ABSTRACT

A composition containing a cooling-sensation imparting substance and a cationic surfactant results in an excellent cooling sensation effect. A composition additionally containing vanilylalkyl ether, wherein the alkyl group has 1 to 6 carbon atoms, is also effective as a composition for improving cooling sensation effect. The present composition for improving cooling sensation effect improves cooling sensation effect while also sustaining that effect. In particular, the present invention provides a composition for improving cooling sensation effect that is able to impart a cooling sensation effect and sustain that effect when used after washing the hair using a shampoo containing no cooling sensation substance or a shampoo containing only a small amount of cooling sensation substance.

8 Claims, 3 Drawing Sheets

COMPOSITION FOR IMPROVING COOLING SENSATION EFFECTS

FIELD OF THE INVENTION

The present invention relates to a composition for improving cooling sensation effect containing a cooling-sensation imparting substance (hereinafter referred to as a cooling sensation substance), a cationic surfactant, and a vanilylalkyl ether as a warm sensation substance in the composition. In addition, the present invention relates to a composition for improving cooling sensation effect under wet conditions, that imparts a strong cooling sensation effect (hereinafter referred to as a wet cooling sensation effect) when used after washing the hair by using, in particular, a shampoo that does not contain a cooling sensation substance, or a shampoo that contains a cooling sensation substance at 0.2 wt % or less. Moreover, the present invention relates to a hair treatment product that contains the above composition. This composition or a product containing this composition has a strong cooling sensation effect while also having the effects of sustaining that cooling sensation effect.

BACKGROUND OF THE INVENTION

There have been considerable changes in lifestyle or consumer needs in recent years. The cosmetics, hair care products, toiletry products, bath additives, pharmaceuticals and various other products used on a daily basis are preferred to impart not only the function inherently required by that product, but also a function that imparts a refreshing sensation during or after use. Consequently, various products impart a refreshing sensation are commercially available in various forms.

Typical examples of products that are preferred to impart a refreshing sensation or cooling sensation effect include cosmetics used in the summer, hair care products such as shampoos, rinses and hair conditioners, body care products such as body shampoos, as well as poultices, bath additives and insect repellent sprays.

In order to satisfy these requirements, conventional types of cooling sensation substances were blended into those products, examples of which include levo-menthol (hereinafter referred to as L-menthol), camphor, methyl salicylate, menthyl malonate, borneol, cineole, menthone, spearmint, peppermint, levo-isopulegol (hereinafter referred to as L-isopulegol), 3-(levo-menthoxy)propane-1,2-diol (hereinafter referred to as 3-(1-menthoxy)propane-1,2-diol), paramenthane-3,8-diol and glycosylmonomenthylorthoacetate.

In order to respond to the growing market for such cooling sensation substances, in addition to research and developing being conducted on novel cooling sensation substances, attempts have been made to combine two or more types of cooling sensation substances in order to enhance cooling sensation effect. Alternatively, research has also been conducted on improving cooling sensation effect by combining cooling sensation substances with other substances.

For example, Japanese Unexamined Patent Publication No. Sho 63-208505 describes the combined use of 3-(1-menthoxy)propane-1,2-diol and a specific glycerin ether, while Japanese Unexamined Patent Publication No. Sho 63-264522 describes the combined use of 3-(1-menthoxy)propane-1,2-diol and hydrophilic polyether denatured silicon, to enhance cooling sensation effect. In addition, a hair treatment composition that uses a combination of a specific cooling sensation substance and a specific warming sensation substance is proposed in Japanese Unexamined Patent Publication No. Hei 6-107527. However, according to these compositions, although a certain degree of increased cooling sensation effect is observed, this can still not be said to be adequate, and the duration of that effect is also not sufficient. Moreover, there is a need for a cooling sensation substance that demonstrates superior cooling sensation effect as well as superior duration of that effect.

Moreover, a cooling sensation composition is proposed in Japanese Unexamined Patent Publication No. 2000-44924. This composition uses the combination of a specific cooling sensation substance and a warming sensation substance in the form of vanilylbutyl ether. A scalp care composition is proposed in Japanese Unexamined Patent Publication No. 2000-191416 that contains a warming sensation substance and a cationic polymer. However, although the former advocates cooling sensation effect, it does not have, as an essential ingredient, the cationic surfactant that is an essential ingredient of the present invention. Although the latter proposes the sustaining of a powerful massage effect and warming sensation on the scalp, there is no description of any cooling sensation effect on the scalp.

OBJECTS AND SUMMARY OF THE INVENTION

Thus, it is an object of the present invention to provide a composition for improving and sustaining a cooling sensation effect.

In addition, it is another object of the present invention to provide a composition for improving and sustaining wet cooling sensation effect.

Moreover, it is still another object of the present invention to provide a hair treatment product that contains a composition for improving cooling sensation effect that sustains that effect. In particular, it is an object of the present invention to provide a hair treatment product that contains a composition for improving wet cooling sensation effect that improves wet cooling sensation effect and sustains that effect.

Briefly stated, the present invention provides a composition containing a cooling-sensation imparting substance and a cationic surfactant which results in an excellent cooling sensation effect. A composition additionally containing vanilylalkyl ether, wherein the alkyl group has 1 to 6 carbon atoms, is also effective as a composition for improving cooling sensation effect. The present composition for improving cooling sensation effect improves cooling sensation effect while also sustaining that effect. In particular, the present invention provides a composition for improving cooling sensation effect that is able to impart a cooling sensation effect and sustain that effect when used after washing the hair using a shampoo containing no cooling sensation substance or a shampoo containing only a small amount of cooling sensation substance.

As a result of an intensive research conducted to solve the above problems, the inventors of the present invention, focusing on cationic surfactants, found that when a hair treatment product composition was prepared that contained a cationic surfactant and the cooling sensation substance, L-menthol, there was an improved cooling sensation effect. For some reason in particular, there was an improved wet cooling sensation effect. Moreover, when the warming sensation substance, vanilylbutyl ether, was blended into the above composition, it was found that the wet cooling sensation effect in particular is improved. It was further found that the resulting effect is sustained, thereby leading to completion of the present invention following additional research.

Namely, the present invention relates to:
1) a composition for improving cooling sensation effect that contains a cooling sensation substance, a cationic surfactant and a vanilylalkyl ether;
2) the above composition for improving cooling sensation effect, wherein the cooling sensation substance is at least one kind of compound selected from the group consisting of L-menthol, isopulegol, 3-(1-menthoxy) propane-1,2-diol and paramenthane-3,8-diol;
3) a hair treatment product having improved cooling sensation effect that contains the above composition for improving cooling sensation effect at 0.001 to 2 wt %;
4) a method for improving cooling sensation effect comprising applying the above composition; and,
5) a hair care product combining a rinse or hair conditioner with a shampoo containing no cooling sensation substance or a shampoo containing a cooling sensation substance at 0.2 wt % or less.

The above, and other objects, features and advantages of the present invention will become apparent from the following description read in conjunction with the accompanying drawings, in which like reference numerals designate the same elements.

The graph shows the cooling sensation effect and duration of cooling sensation effect after washing the hair using only a commercially available tonic shampoo (line A), the cooling sensation effect and duration of cooling sensation effect after treating and washing the hair with Hair Conditioner 1 of the present invention immediately after using a shampoo in which the menthol content was held to 0.1% (line B), and the cooling sensation effect and duration of cooling sensation effect after treating and washing the hair with Hair Conditioner 2 of the present invention immediately after using a shampoo in which the menthol content was held to 0.1% (line C).

Figure 2:
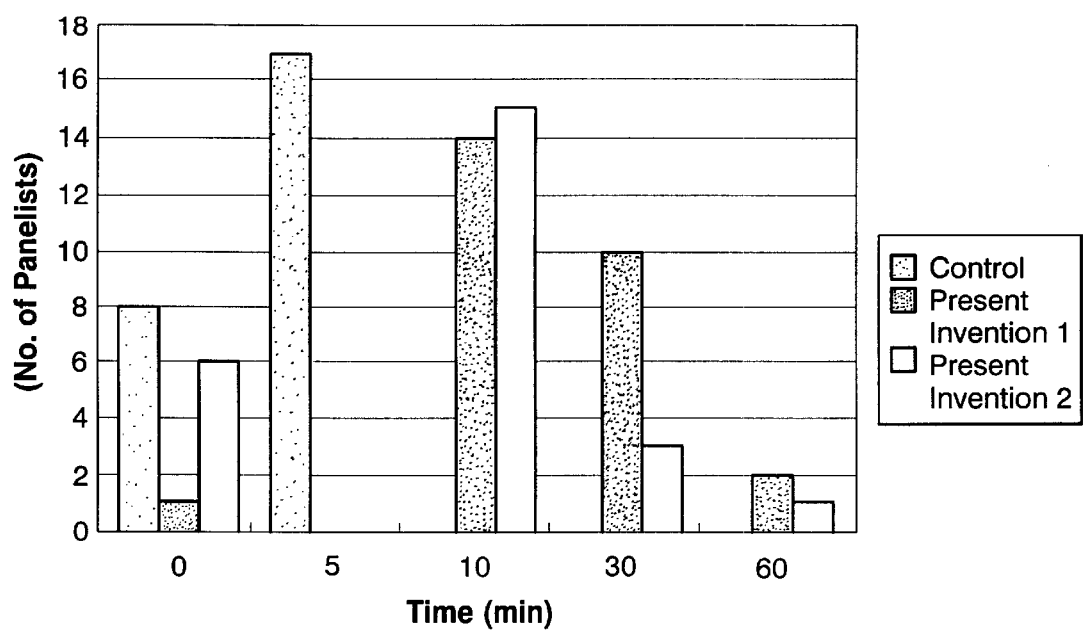

FIG. 2 summarizes the results of sensory evaluations of panelists of the duration of cooling sensation effect in the form of a bar graph when hair has been washed with a shampoo containing no cooling sensation substance followed by treating with a hair conditioner containing the composition for improving cooling sensation effect of the present invention. It should be noted that in the graph, Present Invention 1 refers to treatment of the hair with Hair Conditioner 3 in Example 5, while Present Invention 2 refers to treatment of the hair with Hair Conditioner 2 in Example 5.

Figure 3:
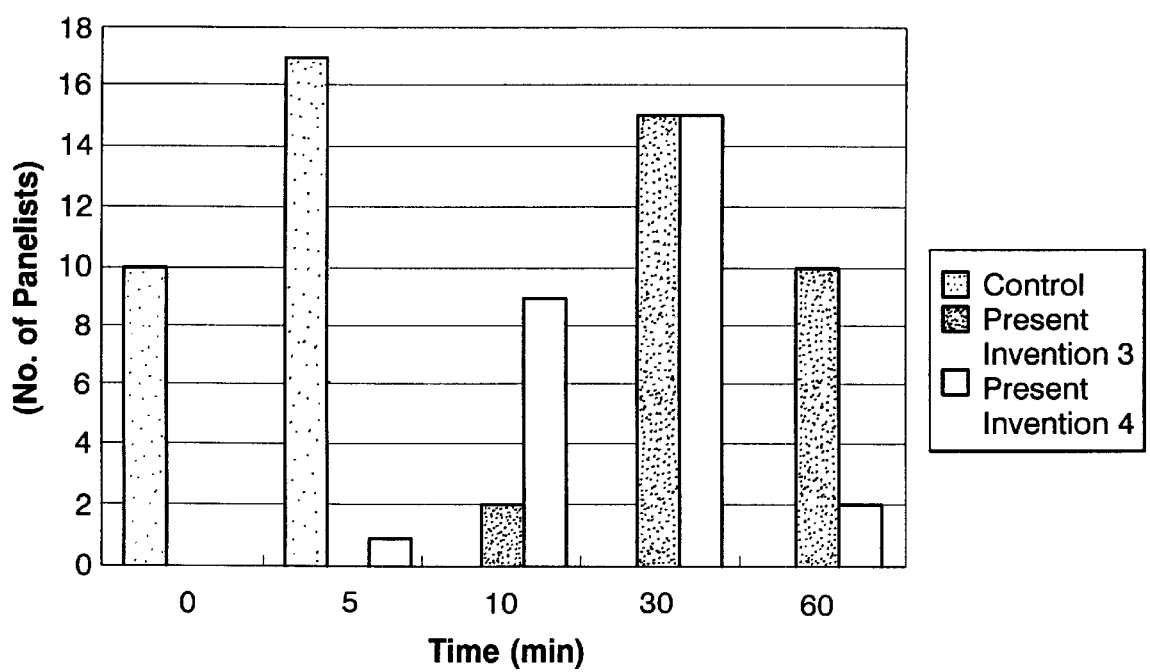

FIG. 3 is a bar graph showing the sensory evaluations of panelists when hair was washed with shampoo containing 0.1% of a cooling sensation substance followed by treating with a hair conditioner containing the composition for improving cooling sensation effect of the present invention. The results are summarized for duration of cooling sensation effect. It should be noted that in the graph, Present Invention 3 refers to treatment of hair with Hair Conditioner 3 in Example 6, while Present Invention 4 refers to treatment of hair with Hair Conditioner 2 in Example 6.

DETAILED DESCRIPTION OF THE INVENTION

The following provides a more detailed explanation of the present invention.

Although any cooling sensation substance known in the prior art may be used for the cooling sensation substance used in the present invention, more preferable examples of cooling sensation substances include L-menthol, L-isopulegol, 3-(1-methoxy)propane-1,2-diol and paramenthane-3,8-diol. These cooling sensation substances may be used alone or in combination with two or more types.

Furthermore, in the case of combining the use of two or more types of the above cooling sensation substances, more preferable effects are obtained if L-menthol is used as an essential ingredient, while using other cooling sensation substances in combination with it.

In addition, the use of L-menthol, L-isopulegol or 3-(1-menthoxy)propane-1,2-diol is particularly desirable for the above cooling sensation substance.

All of these cooling sensation substances are known compounds, and can be easily acquired by conventional methods.

Although varying according to the cooling sensation substance used, the amount of cooling sensation substance used in the present invention is normally from about 0.1 to 0.3 wt %. However, the amount of cooling sensation substance is not limited to this amount. It should be noted that although cooling sensation substances are normally blended into shampoo and so forth at 0.5% or more, and although this brings about a cooling sensation effect, the present invention is characterized by allowing the amount of cooling sensation substance used to be considerably reduced.

An example of a warming sensation substance used in the present invention is a vanilylalkyl ether, in which the alkyl group has from 1 to 6 carbon atoms. In particular, the use of vanilylbutyl ether (VBE), is the most preferable, for both warming sensation and economic effects. These vanilylalkyl ethers are already known warming sensation substances, and are described in, for example, Japanese Patent Publication No. Sho 61-9293.

When a natural warming sensation substance, such as cayenne pepper tincture, capsicin, 8-methyl-N-vanilyl-6-nonanoic amide, nicotinic acid and its derivatives, is used as a warming sensation substance for the purpose of the invention, the obtained composition does not exhibit an improved cooling sensation effect. On the contrary, merely a warming sensation effect may be created in the composition.

The blended amount of vanilylalkyl ether is required to be 0.25 wt % or less in the final product. If the amount in the final product is 0.25 wt % or more, the composition gives the effect of a warming sensation substance instead of the effect of a cooling sensation agent.

The blended amount of vanilylalkyl ether relative to the cooling sensation substance is typically from 1/1000 to 2/1000 parts by weight for L-menthol, or 1/1000 to ½ part by weight for L-isopulegol, 3-(1-menthoxy)propane-1,2-diol and paramenthane-3,8-diol, and preferably 1/200 to 1 part by weight for L-menthol, and 1/1000 to ⅓ part by weight for paramenthane-3,8-diol, while the optimum blending amounts are as shown below.

It should be noted that the optimum blending amounts of vanilylbutyl ether (VBE) shown below are in part(s) by weight corresponding to 1.00 part by weight of cooling sensation substance.

| Cooling sensation substance | VBE optimum blended amount |
| --- | --- |
| L-menthol | 0.01 to 1.00 |
| 3-(1-Menthoxy)propane-1,2-diol | 0.01 to 0.05 |
| L-isopulegol | 0.01 to 0.05 |
| Paramenthane-3,8-diol | 0.001 to 0.01 |

These optimum blended amounts are considered to be dependent on the strength of the cooling sensation of each type of cooling sensation substance.

Cationic surfactants are effective as the surfactant used in the present invention, with quaternary ammonium salts being preferable, and mono-long-chain quaternary ammonium salts or di-long-chain quaternary ammonium salts being particularly preferable. Examples of mono-long-chains or di-long-chains include alkyl groups, alkenyl groups, hydroxyalkyl groups, alkylcarbonylalkyl groups, alkenylcarbonylalkyl groups, alkylaminocarbonylalkyl groups, alkenylaminocarbonylalkyl groups, alkoxyalkyl groups, alkenyloxyalkyl groups, aliphatic acyloxyalkyl groups, alkoxycarbonylalkyl groups and alkenyloxycarbonylalkyl groups.

Specific examples of compounds include distearyldimethyl ammonium chloride, stearyldimethylbenzyl ammonium chloride, stearyltrimethyl ammonium chloride, cetyltrimethyl ammonium chloride, myristyldimethylbenzyl ammonium chloride, lauryldimethylbenzyl ammonium chloride lanolin fatty acid aminopropylethyldimethyl ammonium ethyl sulfate.

These cationic surfactants can be used alone or in any combination of two or more types. The blended amount is preferably 0.1 to 10 wt %, more preferably 1 to 5 wt %, and particularly preferably 3 to 4 wt %, in the composition.

If cationic surfactant is used in an amount greater than 4 wt %, it is economically disadvantageous, while if used in an amount less than 0.1 wt %, it is difficult to obtain the desired effect.

The composition for improving cooling sensation effect of the present invention can be suitably blended with additives used in ordinary cosmetic or, in particular, hair treatment products, in addition to the ingredients mentioned above. Examples of these additives include alcohols, oils, powders, functional beads, capsules, silicones, metal chelating agents, antioxidants, ultraviolet absorbers, humectants, inorganic salts, organic salts and fragrances. However, the compositions of the present invention are not limited to the additives listed here.

The composition for improving cooling sensation effect of the present invention can be prepared by ordinary methods.

Usage examples of the composition for improving cooling sensation effect of the present invention obtained in this manner include products applied to the hair, scalp and skin. In particular, application to so-called hair treatment products such as rinses and hair conditioners or to scalp care products that improve massage effects on the scalp and so forth yield preferable results.

When the above hair treatment products or scalp care products and so forth are used after washing the hair with a shampoo and so forth containing a low amount of menthol or other cooling sensation substance, not only is a pleasant refreshing sensation imparted to the scalp, but that refreshing sensation, namely cooling sensation effect, can be sustained for a long period of time. Moreover, if used after washing the hair with a shampoo and so forth which do not contain menthol or other cooling sensation substance, not only is the invigorating sensation on the scalp improved and a pleasantly dry sensation is imparted to the hair, a suitable cooling sensation effect is also imparted. That refreshing sensation and cooling sensation effect can be sustained for a long period of time.

Thus, in the present invention, a hair care product combining either a hair treatment product, such as rinse or hair conditioner, or a scalp care product and so forth, with a shampoo containing no cooling sensation substance, or with a shampoo containing a cooling sensation substance at 0.2 wt % or less, is included in the present invention.

Namely, a typical example of the combined hair care product is a hair care product that provides, in the form of a single set, a pre-produced shampoo and a pre-produced rinse, hair conditioner or other hair treatment product or scalp care product, but the combined hair care product is naturally not limited to this example. By having the above hair care product on hand and then first washing the hair with a shampoo followed by using a hair treatment product or scalp care product next to it, the invigorating sensation on the scalp is improved, a suitable cooling sensation effect is imparted, and that refreshing sensation and cooling sensation effect can be sustained for a long period of time.

There are no particular restrictions on the preparation forms of the product of the present invention, examples of which include liquids, gels, aerosols and pastes.

EXAMPLES

The following provides a more detailed explanation of the present invention through its examples and reference examples, but the present invention is not limited to these in any way. In addition, unless indicated otherwise, "%" refers to "wt %", and "part(s)" refers to "part(s) by weight".

Reference Example 1

Shampoos containing menthol were prepared having the respective formulation shown below. Each shampoo was used by 15 panelists for 10 days followed by evaluation of cooling sensation effect after use.

| Formulation Example 1 - Formulation Example of Shampoo 1 | |
| --- | --- |
| Purified water | 42.23% |
| [2-Hydroxy-3-(trimethylammonio)propyl] chloride hydroxyethyl cellulose | 0.6 |
| Sodium polyoxyethylene lauryl ether sulfate (3 E.O.) (25%) | 40.0 |
| Disodium polyoxyethylene lauroylethanolamide sulfosuccinate (5 E.O.) | 5.00 |
| 2-Alkyl-N-carboxymethyl-N-hydroxyethylimidazolium betaine | 5.00 |
| Coconut oil fatty acid diethanol amide | 4.00 |
| Glycerin | 0.10 |
| Distearic ethylene glycol | 1.50 |
| Citric acid | 0.22 |
| Potassium chloride | 0.30 |
| Methyl paraoxybenzoate | 0.20 |
| Propyl paraoxybenzoate | 0.10 |
| Ethyl paraoxybenzoate | 0.10 |
| Tetrasodium edetate | 0.05 |
| Fragrance | 0.50 |
| Menthol | 0.10% |

| Shampoo 2 |  |
|---|---|
| Formulation Example 2 - Formulation Example of Shampoo 2 | |
| Purified water | 42.03% |
| [2-Hydroxy-3-(trimethylammonio)propyl] chloride hydroxyethyl cellulose | 0.6 |
| Sodium polyoxyethylene lauryl ether sulfate (3 E.O.) (25%) | 40.0 |
| Disodium polyoxyethylene lauroylethanolamide sulfosuccinate (5 E.O.) | 5.00 |
| 2-Alkyl-N-carboxymethyl-N-hydroxyethylimidazolium betaine | 5.00 |
| Coconut oil fatty acid diethanol amide | 4.00 |
| Glycerin | 0.10 |
| Distearic ethylene glycol | 1.50 |
| Citric acid | 0.22 |
| Potassium chloride | 0.30 |
| Methyl paraoxybenzoate | 0.20 |
| Propyl paraoxybenzoate | 0.10 |
| Ethyl paraoxybenzoate | 0.10 |
| Tetrasodium edetate | 0.05 |
| Fragrance | 0.50 |
| Menthol | 0.20% |

Evaluation Method

Evaluation of cooling sens3ation effect was performed by evaluating to one of five ranks according to the usage evaluation by expert panelists and general panelists.

Rank 5: Cooling sensation felt strongly

Rank 4: Cooling sensation felt

Rank 3: Cooling sensation not felt that much

Rank 2: Cooling sensation hardly felt

Rank 1: Cooling sensation not felt at all

| Evaluation Results | | |
|---|---|---|
| Rank | Shampoo 1 | Shampoo 2 |
| 5 | 0 | 0 |
| 4 | 1 | 1 |
| 3 | 11 | 12 |
| 2 | 1 | 1 |
| 1 | 2 | 1 |

The numbers shown in the column for Shampoos 1 and 2 indicate the number of panelists.

As shown above, the majority of the panelists evaluated both shampoo 1 and shampoo 2 as rank 3 with respect to cooling sensation of the menthol, and there were no large differences observed with respect to the amount of menthol blended in the shampoos.

Example 1

A shampoo containing no menthol was prepared according to formulation example 1 of Reference Example 1. In addition, hair conditioners consisting of the following formulations were prepared that contained the composition for improving cooling sensation effect of the present invention.

After 12 panelists washed their hair with the shampoo, they additionally treated their hair with the hair conditioners indicated below and evaluated the cooling sensation effect after treatment. The hair was washed once a day for 10 days. During the first 5 days, the panelists treated their hair with one of the hair conditioners, and during the last 5 days, they treated their hair with the other hair conditioner. Cooling sensation effect was evaluated following treatment for 5 days.

| Formulation Example 3 - Hair Conditioner 1 | |
|---|---|
| Purified water | 42.03 parts |
| [2-Hydroxy-3-(trimethylammonio)propyl] chloride hydroxyethyl cellulose | 0.200 |
| Sodium hydroxide | 0.005 |
| Methyl paraoxybenzoate | 0.20 |
| Propyl paraoxybenzoate | 0.10 |
| Tetrasodium edetate | 0.05 |
| Polyoxyethylene cetyl ether | 0.500 |
| Cetanol | 2.000 |
| Behenyl alcohol | 2.000 |
| Stearyltrimethyl ammonium chloride | 3.000 |
| Distearyldimethyl ammonium chloride | 0.200 |
| Cetyl 2-ethylhexanoate | 0.500 |
| Methylpolysiloxane | 2.000 |
| Fragrance | 0.500 |
| Menthol | 0.100 |
| Vanilylbutyl ether | 0.050 |

| Formulation Example 4 - Hair Conditioner 2 | |
|---|---|
| Purified water | 42.03 parts |
| [2-Hydroxy-3-(trimethylammonio)propyl] chloride hydroxyethyl cellulose | 0.200 |
| Sodium hydroxide | 0.005 |
| Methyl paraoxybenzoate | 0.20 |
| Propyl paraoxybenzoate | 0.10 |
| Tetrasodium edetate | 0.05 |
| Polyoxyethylene cetyl ether | 0.500 |
| Cetanol | 2.000 |
| Behenyl alcohol | 2.000 |
| Stearyltrimethyl ammonium chloride | 3.000 |
| Distearyldimethyl ammonium chloride | 0.200 |
| Cetyl 2-ethylhexanoate | 0.500 |
| Methylpolysiloxane | 2.000 |
| Fragrance | 0.500 |
| Menthol | 0.100 |
| Menthoxypropane-1,2-diol | 0.200 |

Evaluation Method

Evaluation was performed in the same manner as the method described in the reference examples.

| Evaluation Results | | |
|---|---|---|
| Rank | Hair Conditioner 1 | Hair Conditioner 2 |
| 5 | 5 | 1 |
| 4 | 3 | 6 |
| 3 | 2 | 3 |
| 2 | 1 | 1 |
| 1 | 1 | 1 |

The numbers shown in the column for Hair Conditioners 1 and 2 indicate the number of panelists.

As shown in the above results, when the hair was washed with a hair conditioner as shown in Formulation 3 or 4 after washing the hair with a shampoo containing no menthol (cooling sensation substance), a pleasant cooling sensation effect was able to be obtained, with 70% of the panelists recognizing a cooling sensation effect. Since there is no cooling sensation effect after washing the hair with a shampoo containing no menthol (cooling sensation substance), the composition for improving cooling sensation effect of the present invention was determined to have a superior cooling sensation effect.

Example 2

The shampoo of Formulation 2 in Reference Example 1, and the hair conditioner containing the composition for improving cooling sensation effect described in Example 1 was used.

Hair was treated with shampoo and hair conditioner by 10 panelists in the same manner as Example 1 followed by evaluation of cooling sensation effect after treatment.

| | Evaluation Results | |
|---|---|---|
| Rank | Hair Conditioner 1 | Hair Conditioner 2 |
| 5 | 7 | 4 |
| 4 | 2 | 5 |
| 3 | 0 | 0 |
| 2 | 1 | 1 |
| 1 | 0 | 0 |

The numbers shown in the column for Hair Conditioners 1 and 2 indicate the number of panelists.

As shown in the above results, when the hair was washed with a hair conditioner like that indicated in Formulation Examples 3 and 4 after washing the hair with shampoo containing 0.2% menthol, a pleasant cooling sensation effect was able to be obtained. When considering that a significant cooling sensation effect is unlikely to be perceived when washing the hair with shampoo containing 0.2% menthol, the composition for improving cooling sensation effect of the present invention was determined to have a superior cooling sensation effect.

Example 3

Cooling Sensation Effect Duration Test

A shampoo containing menthol (blended amount: 0.1%) was prepared in accordance with Formulation Example 1 in Reference Example 1, and the hair conditioner described in Example 1 was prepared.

Twenty-five panelists in their thirties to their fifties washed their hair with the shampoo and then treated their hair with Hair Conditioner 1 followed by an evaluation of the duration of the cooling sensation effect following treatment. It should be noted that treatment only with a commercially available tonic shampoo (produced by Sunstar; menthol was blended in an amount of 0.7%) was used for the control (comparative example).

Evaluation Method

Evaluation of cooling sensation effect was evaluated by the panelists according to the time when the cooling sensation effect was felt to have reached a peak, and whether or not a cooling sensation effect is felt.

| Evaluation Results | | |
|---|---|---|
| Cooling Sensation Effect | Control | Example 3 |
| 1) Immediately disappeared | 0 | 0 |
| 2) Felt a peak after about 2 minutes and disappeared 5 minutes later | 25 | 5 |
| 3) Felt a peak after about 4 to 5 minutes; and disappeared 10 to 20 minutes later | 0 | 20 |

The numbers indicate the number of panelists.

Item 2) of the above result indicates the total number of those panelists who felt a peak in cooling sensation effect after about 2 minutes, and those panelists who evaluated cooling sensation effect as disappearing after about 5 minutes.

Item 3) of the above result indicates the total number of those panelists who felt a peak in cooling sensation effect after about 4 to 5 minutes, and those panelists who evaluated cooling sensation effect as disappearing after about 10 to 20 minutes.

Figure 1:
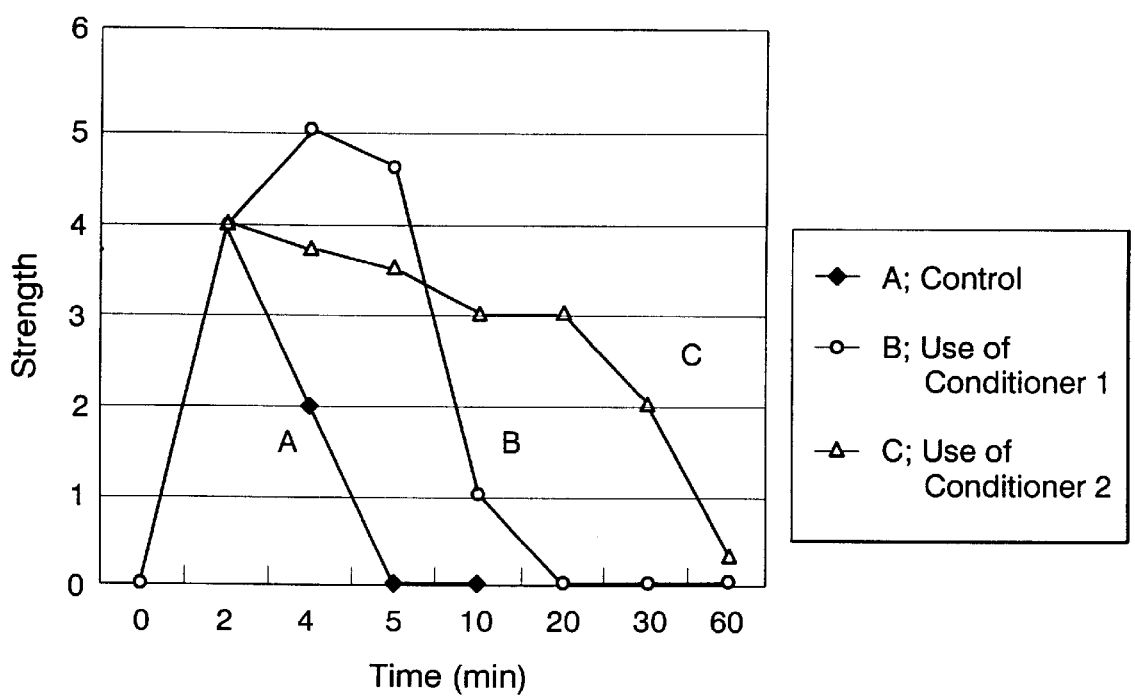
FIG. 1 shows the sensory evaluations of panelists in the form of a line graph when hair was washed with shampoo containing 0.1% of a cooling sensation substance followed by treating with a hair conditioner containing the composition for improving cooling sensation effect of the present invention. The vertical axis indicates the relative strength of the cooling sensation effect.

As indicated by line A (control) in FIG. 1, in the case of using only commercially available tonic shampoo, cooling sensation effect disappeared after about 5 minutes. In contrast, cooling sensation effect and the duration of cooling sensation effect after treating and washing the hair with Hair Conditioner 1 prepared from the composition for improving cooling sensation effect of the present invention immediately after using a shampoo in which the menthol content was held to 0.1% continued for 4 to 5 minutes after washing the hair as shown by line B in FIG. 1, while cooling sensation effect disappeared after 20 minutes. In other words, the duration of cooling sensation effect of hair treatment products containing the composition for improving cooling sensation effect of the present invention was determined to be extremely good.

Example 4

Cooling Sensation Effect Duration Test

With the exception of substituting Hair Conditioner 2 for Hair Conditioner 1 in Example 3, a test was conducted in the same manner as Example 3. Twenty-seven panelists conducted the same sensory evaluation as Example 3. The evaluation results of the panelists are shown below.

| Evaluation Results | |
|---|---|
| Cooling sensation effect | Example 4 |
| 1) Immediately disappeared | 2 |
| 2) Disappeared after about 10 minutes | 13 |
| 3) Disappeared after about 30 minutes | 10 |
| 4) Disappeared after about 60 minutes | 2 |

As shown by line A in FIG. 1, in the case of using only a commercially available tonic shampoo, cooling sensation effect disappeared after about 5 minutes. In contrast, cooling sensation effect and the duration of cooling sensation effect after treating and washing the hair with Hair Conditioner 2 prepared from the composition for improving cooling sensation effect of the present invention immediately after using a shampoo in which the menthol content was held to 0.1% continued for 4 to 5 minutes after washing the hair as shown by line C in FIG. 1, while cooling sensation effect disappeared after 60 minutes. In other words, the duration of cooling sensation effect of hair treatment products containing the composition for improving cooling sensation effect of the present invention was determined to be extremely good.

Example 5

Cooling Sensation Effect Duration Test

Hair Conditioner 3 was prepared containing the composition for improving cooling sensation effect of the present invention in accordance with Formulation Example 5 described below. Hair was treated with Hair Conditioner 3 and Hair Conditioner 2 after washing the hair with the shampoo containing no menthol used in Example 1. The duration of cooling sensation effect felt after treatment was evaluated by a sensory evaluation in the same manner as Example 3. There were 25 panelists in their thirties to their fifties.

| Formulation Example 5-Formulation of Hair Conditioner 3 | |
| --- | --- |
| Purified water | 42.03 parts |
| [2-Hydroxy-3-(trimethylammonio)propyl] chloride hydroxyethyl cellulose | 0.200 |
| Sodium hydroxide | 0.005 |
| Methyl paraoxybenzoate | 0.20 |
| Propyl paraoxybenzoate | 0.10 |
| Tetrasodium edetate | 0.05 |
| Polyoxyethylene cetyl ether | 0.500 |
| Cetanol | 2.000 |
| Behenyl alcohol | 2.000 |
| Stearyltrimethyl ammonium chloride | 3.000 |
| Distearyldimethyl ammonium chloride | 0.200 |
| Cetyl 2-ethylhexanoate | 0.500 |
| Methylpolysiloxane | 2.000 |
| Fragrance | 0.500 |
| Menthol | 0.100 |
| Menthoxypropane-1,2-diol | 0.200 |
| Vanilylbutyl ether | 0.05 |

| Evaluation Results | | | |
| --- | --- | --- | --- |
| Cooling sensation effect | Comparative Example | Present Invention 1 | Present Invention 2 |
| 1) Immediately disappeared | 8 | 6 | 0 |
| 2) Disappeared after about 5 minutes | 17 | 0 | 0 |
| 3) Disappeared after about 10 minutes | 0 | 15 | 14 |
| 4) Disappeared after about 30 minutes | 0 | 3 | 10 |
| 5) Disappeared after about 1 hour | 0 | 1 | 1 |

Present Invention 1 refers to treatment of the hair with Hair Conditioner 3, while Present Invention 2 refers to treatment of the hair with Hair Conditioner 2. The control (comparative example) was the same as in Example 3.

Referring to FIG. 2, in the case of using only commercially available tonic shampoo, cooling sensation effect disappeared after about 5 minutes. In contrast, when the cooling sensation effect and the duration of cooling sensation effect were evaluated after treating and washing the hair with Hair Conditioner 3 or Hair Conditioner 2 prepared from the composition for improving cooling sensation effect of the present invention immediately after using a shampoo containing no menthol, as shown in the bar graph of FIG. 2, cooling sensation effect was still observed even after 10–30 minutes had elapsed after washing the hair. In other words, the duration of cooling sensation effect of hair treatment products containing the composition for improving cooling sensation effect of the present invention was determined to be extremely good.

Example 6

Cooling Sensation Effect Duration Test

Hair was treated with Hair Conditioner 3 described in Example 5 and Hair Conditioner 2 after washing the hair with Shampoo 1 (containing 0.1% menthol) described in Reference Example 1. The duration of cooling sensation effect felt after treatment was evaluated by a sensory evaluation in the same manner as Example 3. There were 27 panelists in their thirties to their fifties.

| Evaluation Results | | | |
| --- | --- | --- | --- |
| Cooling sensation effect | Comparative Example | Present Invention 3 | Present Invention 4 |
| 1) Immediately disappeared | 10 | 0 | 1 |
| 2) Disappeared after about 5 minutes | 17 | 0 | 0 |
| 3) Disappeared after about 10 minutes | 0 | 2 | 14 |
| 4) Disappeared after about 30 minutes | 0 | 15 | 10 |
| 5) Disappeared after about 1 hour | 0 | 10 | 2 |

Present Invention 3 refers to treatment of the hair with Hair Conditioner 3, while Present Invention 4 refers to treatment of the hair with Hair Conditioner 2. The control (comparative example) was the same as in Example 3.

Referring to FIG. 3, in the case of using only-commercially available tonic shampoo, cooling sensation effect disappeared after about 5 minutes. In contrast, as shown in the bar graph of FIG. 3, cooling sensation effect after treating and washing the hair with Hair Conditioner 3 and Hair Conditioner 2 described above immediately after using a shampoo in which the menthol content was held to 0.1% was felt for 4 to 6 minutes after washing the hair, and the duration of cooling sensation effect lasted for 60 minutes after washing the hair, at which time it disappeared. In other words, the duration of cooling sensation effect of hair care products containing the composition for improving cooling sensation effect of the present invention was determined to be extremely good.

As described above, the present invention enables a cooling sensation effect not present in the prior art to be felt, and enables that cooling sensation effect to be sustained. Moreover, a cooling sensation effect and refreshing effect can be imparted for a long period of time by using these techniques in hair treatment products such as shampoos, hair conditioners and hair tonics. In other words, the composition for improving cooling sensation effect of the present invention was able to impart an invigorating sensation to the scalp during application, and that invigorating sensation was able to be sustained for a long period of time even after drying the head with a towel and so forth.

More specifically, the amount of cooling sensation substance used in hair care products of the prior art normally consisted of a menthol content of 0.5% or more even in the case of tonic shampoos using menthol as the cooling sensation substance. Although a cooling sensation effect is known to be felt when this tonic shampoo is used, on the other hand, it also is intensely irritating to the eyes and skin, while also having the disadvantage of presenting a masculine image. Therefore, when the amount of menthol used was attempted to be reduced, the result was that the shampoo no longer allowed the obtaining of satisfying cooling sensation effect in the case of shampooing.

However, when, after washing the hair with a shampoo containing no cooling sensation substance, the hair was treated with a composition for improving cooling sensation effect, which was produced by adding menthol, another type of cooling sensation substance (e.g., menthoxypropane-1,2-diol) and cationic surfactant, and when the hair was treated with the composition for improving cooling sensation effect of the present invention containing menthol, warming effect substance (VBE) and cationic surfactant, a cooling sensation effect was surprisingly able to be obtained unlike anything in the past (Example 1).

In addition, cooling sensation effect was clearly determined to be enhanced in the case of adding not a cooling sensation substance, but rather a warming sensation substance in the form of vanilylalkyl ether, in order to enhance the cooling sensation of menthol. Moreover, cooling sensation effect was determined to be increased remarkably for shampooed hair as a result of additionally using the composition for improving cooling sensation effect of the present invention employing such a combination (Examples 3, 4, 5 and 6).

Moreover, since a hair treatment using primarily a cationic surfactant is more effective for obtaining stimulation (cooling sensation effect) than shampoo using primarily anionic surfactant, an even greater cooling sensation effect was able to be imparted by using a hair conditioner containing a cationic surfactant after first providing a certain degree of stimulation with shampoo. Namely, a hair care system was able to be formulated that imparts an efficient cooling sensation effects by reducing the amount of menthol blended into the shampoo.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A hair care product having a cooling sensation effect comprising from about 0.001 to about 2 wt % of a composition comprising:
    (a) a cooling-sensation imparting substance;
    (b) a cationic surfactant selected from the group consisting of distearyldimethyl ammonium chloride, stearyldimethylbenzyl ammonium chloride, stearyltrimethyl ammonium chloride, cetyltrimethyl ammonium chlroride, myristyldimethylbenzyl ammonium chloride, lauryldimethylbenzyl ammonium chlroride, lanolin fatty acid and aminopropylethyldimethyl ammonium ethyl sulfate; and
    (c) a vanilylalkyl ether, wherein the alkyl group of said vanilylalkyl ether has from 1 to 6 carbon atoms.

2. The hair care product having a cooling sensation effect according to claim 1, wherein said cooling-sensation imparting substance is a mixture of levo-menthol and at least one compound selected from the group consisting of levo-isopulegol, 3-(levo-menthoxy)propane-1,2-diol and paramenthane-3,8-diol.

3. The hair care product according to claim 1, further comprising a shampoo containing no cooling-sensation imparting substance or shampoo containing a cooling-sensation imparting substance at 0.2 wt % or less.

4. The hair care product of claim 1, wherein the cationic surfactant is present in from about 0.1 to about 10 wt %.

5. The hair care product of claim 1, wherein the vanilylalkyl ether is present from about 0.001 to about 1 part by weight with respect to 1.0 part by weight of said cooling-sensation imparting substance.

6. The hair care product of claim 1, wherein the hair care product is a hair conditioner.

7. The hair care product of claim 1, wherein the hair care product is a hair rinse.

8. A hair rinse or hair conditioner for application to hair after application of a shampoo containing no more than about 0.2 wt % of a cooling sensation imparting substance, the hair rinse or hair conditioner comprising from about 0.001 to about 2 wt % of a composition comprising:
    (a) a cooling-sensation imparting substance;
    (b) a cationic surfactant selected from the group consisting of distearyldimethyl ammonium chloride, stearyldimethylbenzyl ammonium chloride, stearyltrimethyl ammonium chloride, cetyltrimethyl ammonium chlroride, myristyldimethylbenzyl ammonium chloride, lauryldimethylbenzyl ammonium chlroride, lanolin fatty acid and aminopropylethyldimethyl ammonium ethyl sulfate; and
    (c) a vanilylalkyl ether, wherein the alkyl group at the vanilylalkyl ether has form 1 to 6 carbon atoms.

* * * * *

UNITED STATES PATENT AND TRADEMARK OFFICE
CERTIFICATE OF CORRECTION

PATENT NO.    : 6,544,535 B2  
DATED         : April 8, 2003  
INVENTOR(S)   : Kazutoshi Sakurai It is certified that error appears in the above-identified patent and that said Letters Patent is hereby corrected as shown below:

<u>Title page,</u>
Item [30], please insert:
-- Foreign Application Priority Data
October 10, 2000 [JP] ........................ 2000-308871 --

Signed and Sealed this

Twenty-third Day of September, 2003

JAMES E. ROGAN
*Director of the United States Patent and Trademark Office*